(12) United States Patent
Suda et al.

(10) Patent No.: US 8,815,176 B2
(45) Date of Patent: Aug. 26, 2014

(54) TEMPERATURE-SENSITIVE INDICATOR

(75) Inventors: Hiroshi Suda, Saitama (JP); Susumu Mikami, Saitama (JP); Tetsuya Nishimura, Tokyo (JP)

(73) Assignee: Nippon Thermostat Co., Ltd., Tokyo (JP)

( * ) Notice: Subject to any disclaimer, the term of this patent is extended or adjusted under 35 U.S.C. 154(b) by 558 days.

(21) Appl. No.: 13/147,144

(22) PCT Filed: Dec. 1, 2009

(86) PCT No.: PCT/JP2009/006511
§ 371 (c)(1),
(2), (4) Date: Jul. 29, 2011

(87) PCT Pub. No.: WO2010/086937
PCT Pub. Date: Aug. 5, 2010

(65) Prior Publication Data
US 2011/0280775 A1    Nov. 17, 2011

(30) Foreign Application Priority Data

Jan. 29, 2009    (JP) ................................. 2009-017414

(51) Int. Cl.
| | |
|---|---|
| *G01N 31/22* | (2006.01) |
| *G01N 25/00* | (2006.01) |
| *G01K 1/02* | (2006.01) |
| *G01K 3/04* | (2006.01) |
| *G01K 1/16* | (2006.01) |
| *G01N 33/52* | (2006.01) |

(52) U.S. Cl.
CPC .. *G01K 3/04* (2013.01); *G01K 1/02* (2013.01); *G01N 31/229* (2013.01); *G01N 33/525* (2013.01); *G01K 1/16* (2013.01)
USPC ......... 422/424; 422/82.12; 116/216; 116/219

(58) Field of Classification Search
CPC ....... G01N 25/00; G01N 21/75; G01N 31/22; G01N 31/229; G01N 33/52; G01N 33/525; G01K 1/02; G01K 11/12
USPC .................. 422/424, 82.12; 116/216, 219
See application file for complete search history.

(56) References Cited

U.S. PATENT DOCUMENTS 3,243,303 A * 3/1966 Johnson ........................ 426/88

FOREIGN PATENT DOCUMENTS

| JP | 2028418 Y | 7/1990 |
| JP | 2008-170202 A | 7/2008 |

*Primary Examiner* — Lore Jarrett
(74) *Attorney, Agent, or Firm* — Orion Consulting, Ltd.; Joseph P. Farrar, Esq.

(57) ABSTRACT

Provided is a temperature sensitive indicator, which can be held in a desired state and is not affected by temperature of a finger at the time of an operation of the temperature sensitive indicator. The temperature sensitive indicator includes: a member base (13) including an upper base member (11) and a lower base member (12); and a label component (21) sandwiched and held between the upper base member and the lower base member of the member base under a state in which a pulled-out portion on one end side of the label component is protruded outward. By pulling one end of the label component out of the member base, a capsule (28) is pressed in a convex portion (16) provided on any one of or both of the upper base member and the lower base member and is broken to enter a preparatory state for measurement, and a temperature sensitive material melts at a predetermined temperature or more so as to be absorbed by an absorbent paper (23), enabling confirmation of a fact that the temperature sensitive indicator senses a set temperature or more through confirmation of color development of the absorbent paper.

2 Claims, 4 Drawing Sheets

TEMPERATURE-SENSITIVE INDICATOR

TECHNICAL FIELD

The present invention relates to a temperature sensitive indicator for irreversibly indicating whether a temperature of a portion to be subjected to temperature sensing reaches to a predetermined temperature or more or a predetermined temperature or less, and more particularly, to a temperature sensitive indicator capable of visually confirming at a glance whether or not a portion to be subjected to temperature sensing is exposed to an environment of a predetermined temperature or more or a predetermined temperature or less.

BACKGROUND ART

In recent years, temperature control has been important in quality control of commercial items and products. For example, when fresh products such as fresh food and cut flowers, medical goods, and semiconductor materials are exposed to a predetermined temperature or more without undergoing sufficient temperature control, quality of those commercial items and products may be lowered or degraded, and bacteria may grow, causing rottenness.

For this reason, strict temperature control is necessary not only at the time of production of those commercial items and products but also at the time of delivery and storage of the same, and a temperature sensitive indicator is used as means for continuously monitoring the temperature control.

As such a temperature sensitive indicator, one having the following structure has been conventionally proposed. Specifically, the protruding space is provided in part of the label-like piece, and the capsule containing the temperature sensitive material is embedded inside the protruding space. In addition, the label-like piece is pasted to an object to be measured under a state in which the capsule is pressed and broken with a finger or the like. Consequently, it is possible to confirm whether or not the object to be measured is exposed to the environment of the predetermined temperature or more or the predetermined temperature or less (for example, see Patent Literature 1).

However, the above-mentioned temperature sensitive indicator of Patent Literature 1 has the structure in which the capsule is broken with a finger or the like when pasted to the object to be measured, and hence the temperature of the finger or the like may affect the temperature sensitive material contained in the capsule.

For this reason, as the temperature sensitive indicator of this kind, one having the following configuration has been proposed. Specifically, by pulling out the capsule portion through the gap of the capsule breaking means, the capsule can be broken in a state of being free from the effect of temperature (for example, see Patent Literature 2).

CITATION LIST

Patent Literature 1: Japanese Utility Model Examined Publication No. Hei 2-28418
Patent Literature 2: Japanese Patent Application Laid-open No. 2008-170202

SUMMARY OF INVENTION

Technical Problem

However, in the above-mentioned temperature sensitive indicator of Patent Literature 2, it is necessary to perform such a troublesome work that the label-like indicator is pulled out through the gap of the capsule breaking means, and there are problems with workability during assembly, such as a problem in that it is troublesome to set the indicator to the capsule breaking means.

The present invention has been made in view of the above-mentioned problem, and an object of the present invention is therefore to obtain a temperature sensitive indicator, which is not affected by temperature of a finger or the like at the time of an operation of the temperature sensitive indicator, and is excellent in assembly property and also in usability.

Solution to Problem

In order to achieve the above-mentioned object, a temperature sensitive indicator according to the present invention (invention according to claim 1) includes: a member base including an upper base member and a lower base member; and a label component sandwiched and held between the upper base member and the lower base member of the member base under a state in which a pulled-out portion on one end side of the label component is protruded outward, the label component including: a sheet member; an absorbent member provided on an upper part of the sheet member; a capsule placed on one end side of the absorbent member and containing a temperature sensitive material that melts at a predetermined temperature or more; and a cover member including a protrusion covering the capsule, in which the protrusion of the cover member is held inside the member base in a state of being housed in a convex portion provided on any one of or both of the upper base member and the lower base member, and in which, by pulling one end of the label component out of the member base, the capsule is pressed in the convex portion of the lower base member and is broken to enter a preparatory state for measurement, and the temperature sensitive material melts into a liquid at the predetermined temperature or more so that the liquid is absorbed by the absorbent member, enabling confirmation of a fact that the temperature sensitive indicator senses a set temperature or more through confirmation of color development of the absorbent member.

In the temperature sensitive indicator of the present invention (invention according to claim 2) as described in claim 1, the label component includes a plurality of label components set in the member base, and one of the plurality of label components is pulled out for use, and is attached to an object to be measured.

The temperature sensitive indicator of the present invention (invention according to claim 3) as described in claim 1 or 2 further includes a bent portion provided between the convex portion of the member base and a side end portion of the member base from which the pulled-out portion of the label component is protruded.

In the temperature sensitive indicator of the present invention as described in claim 1, 2, or 3, the label component includes a window portion formed on another end side of the absorbent member, for allowing confirmation of a state of color development of the absorbent member, enabling confirmation of a fact that the temperature sensitive indicator senses the predetermined temperature and a lapse of time during the sensing through the confirmation of the state of color development through the window portion.

Advantageous Effects of Invention

As described above, according to the temperature sensitive indicator of the present invention, the member base including the upper base member and the lower base member is used as a case for storage, and the label component is pulled out of the member base for use. Thus, the capsule is broken to enter the preparatory state for measurement. Therefore, despite the simple configuration, unlike the conventional case, it is not necessary to crush and break the capsule with a finger or the like when setting the temperature sensitive indicator, and the temperature of the finger or the like does not affect the temperature sensitive material, which is greatly effective in enabling more precise temperature measurement.

Further, according to the present invention, in the member base, the convex portion for holding and protecting the capsule is formed integrally with the lower base member, which is advantageous in enabling a reduction of the number of components, etc. Moreover, the convex portion of the member base has such a functional advantage as to have two functions: holding and protection of the capsule on the label component side; and breaking the capsule.

Further, according to the present invention, the plurality of label components are held in parallel to one another in the member base, and the label components become usable by pulling out the required number of the label components for use. Consequently, the member base is increased in size, and hence there is an advantage in that rigidity of the case is increased and the member base is easily held by hand when pulling out the label component. In addition, the member base does not need to be discarded for each label component, which is advantageous in enabling a reduction of scraps.

Further, according to the present invention, the bent portion is provided in such a direction as to cross the label component of the member base. Consequently, the rigidity of the member base is increased, and a degree of adhesion between the upper base member and the lower base member is improved. In addition, there is an advantage in that a clearance (gap) is eliminated even when reducing bonding portions between the upper base member and the lower base member.

Moreover, the capsule, which has not been able to be broken in the above-mentioned convex portion when pulling out the label component, can also be broken reliably by causing the label component to pass through the bent portion, which is advantageous in enabling the capsule to be broken more reliably.

Further, according to the present invention, at the set temperature or more, the internal temperature sensitive material (wax, etc.) melts to develop color such as red, and it is possible to know the lapse of time based on a range (distance) at which the temperature sensitive material permeates the absorbent member (permeable material) of the label component. That is, even if the absorbent member partially develops color, there is no problem if the color development indicates that the lapse of time is within a certain range, and its confirmation can be performed. Further, the label component is formed by pasting a nontransparent and opaque sheet on part of the surface of the label component made of a transparent material. However, by making part of the opaque sheet transparent (forming the window portion), it is possible to confirm color development of the temperature sensitive material absorbed by the absorbent member, and to confirm the fact that the certain period of time or more elapses.

DESCRIPTION OF EMBODIMENT

Figure 1:
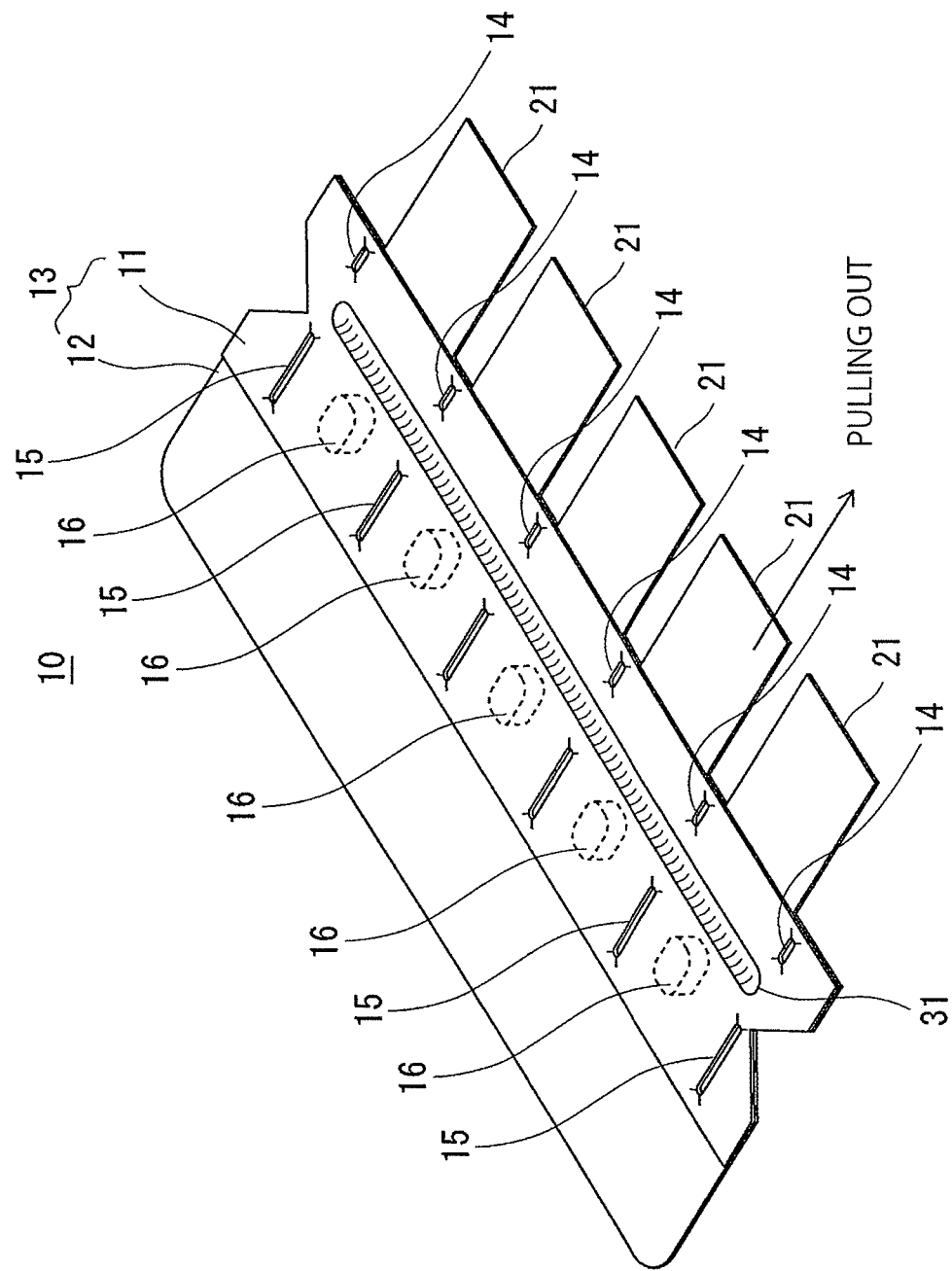
FIG. 1 A schematic perspective view of a temperature sensitive indicator according to an embodiment of the present invention.
Figure 2:
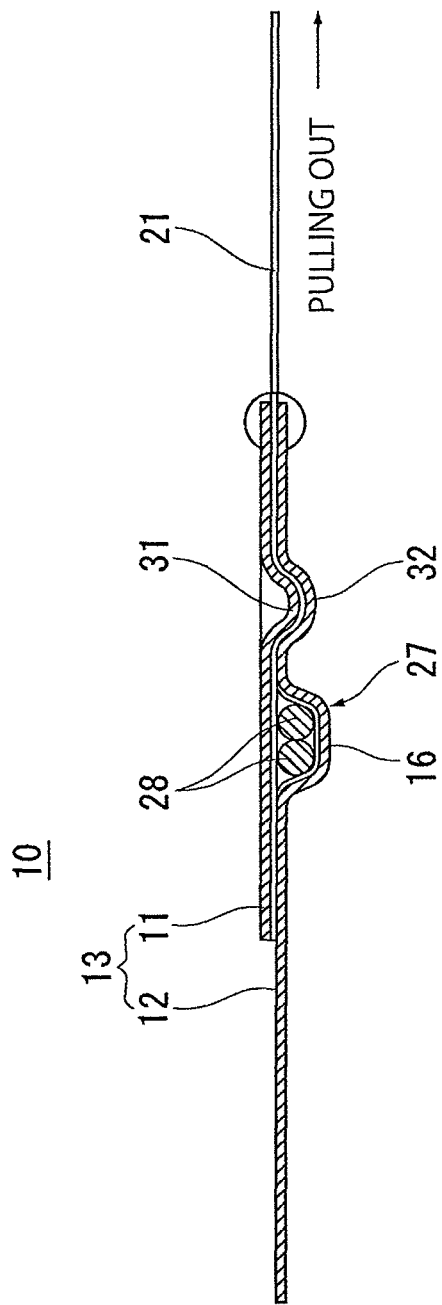
FIG. 2 A schematic side cross-sectional view of the temperature sensitive indicator of FIG. 1.
Figure 3:
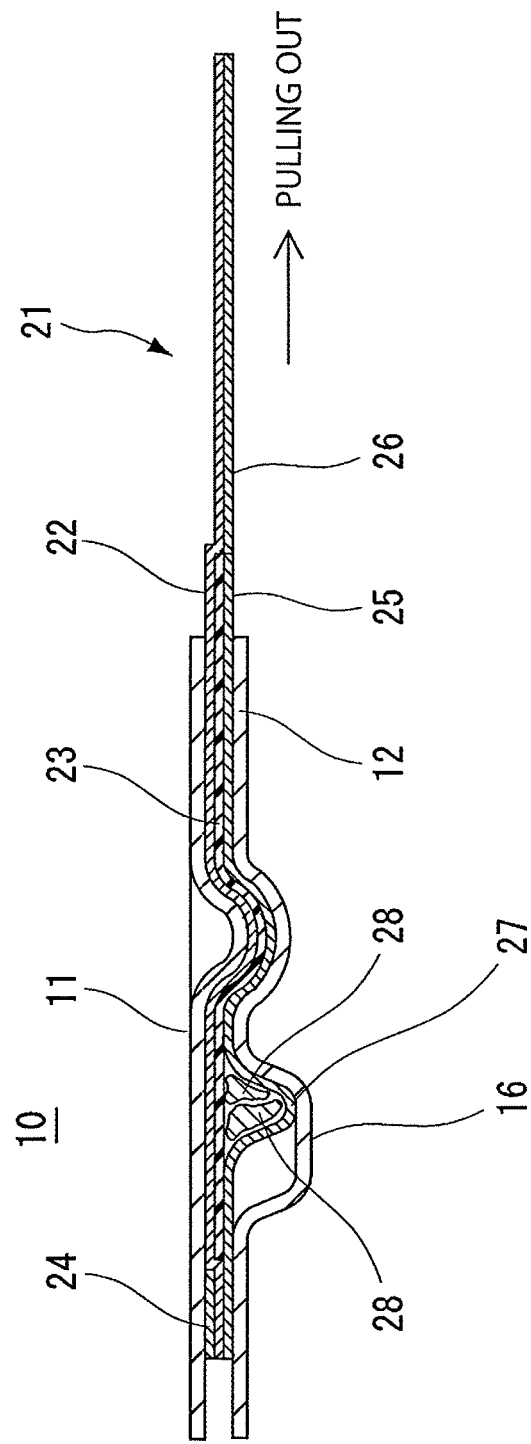
FIG. 3 A schematic cross-sectional view illustrating a state when a label component is drawn out for use in the temperature sensitive indicator of FIG. 1 and FIG. 2.

FIG. 1 to FIG. 3 illustrate a temperature sensitive indicator according to an embodiment of the present invention. In the figures, a temperature sensitive indicator 10 includes a member base 13 including an upper base member 11 and a lower base member 12, and a plurality of (five, in this case) label components 21 held in a state of being sandwiched therebetween.

Here, as is apparent from FIG. 1 to FIG. 3, each of the label components 21 described above includes a long sheet member 22 formed of a transparent sheet, an absorbent paper (permeable material) 23 as an absorbent member having a predetermined length and provided on a lower surface side of the sheet member 22 by being pasted thereon, etc., capsules 28 placed on one end side of the absorbent paper 23 and each containing a temperature sensitive material melting at a predetermined temperature or more (for example, liquid containing a dye and a wax melting at a certain temperature), and an upper cover member (opaque sheet, in this case) 25 including a protrusion forming portion (protruding portion) 27 covering the capsules 28.

Further, in FIG. 3, reference numeral 24 denotes a cover piece formed of an opaque sheet pasted on the front side surface of the sheet member 22 from an opposite drawn-out-portion side to a position of a predetermined length in each of the label components 21, and reference numeral 26 denotes a release paper pasted on the back surface side of the sheet member 22 from a drawn-out end side, for exposing a pasting portion formed of an adhesive layer when the label component is set to an object to be measured or the like.

Here, the label component 21 as described above only needs to have a label structure as the temperature sensitive indicator having a conventionally well-known structure. In other words, the label component 21 only needs to have such a shape as to allow the label to be pinched and pulled out by hand, and include the protruding portion 27 bulging on part of the label component 21 on its lower surface side so as to receive the capsules 28 containing the temperature sensitive material in the protruding portion for holding and protection.

Note that, as the temperature sensitive material filling the capsules 28, for example, a so-called colored wax in which an oil-soluble pigment, colorant, or dye is mixed with a solid solution made of linear hydrocarbon or a composition of linear hydrocarbon can be used. Further, as the temperature sensitive material, a chemical substance that melts or discolors at a predetermined temperature may be used. Further, a colored gel or the like that changes to a liquid phase at a predetermined temperature or less can be used. In addition, a temperature sensitive material having two or more melting points (coagulation points), which keeps its solid state within a range of predetermined temperatures and enters a liquid state at a lower limit temperature or less and an upper limit temperature or less of the predetermined temperatures can be used as well.

As described above, the temperature sensitive indicator using the colored gel that changes to a liquid phase at a predetermined temperature or less can be suitably used in commercial items or products such as lettuces, potatoes, bean curd, and carbonated beverages (beer), which are degraded in quality at the time of freezing.

Further, the absorbent paper 23 only needs to be absorbable and permeable to the temperature sensitive material, and a conventionally used filter paper, porous body (film, sponge, etc.), silica gel, and the like can be used.

The absorbent paper 23 is formed into substantially a strip-like shape in plan view, and on its one end side, the protruding portion 27 for holding and protecting the capsules 28 is situated. Further, the other end of the absorbent paper 23 is exposed to the outside from the end portion of the cover member 24, to thereby serve as a temperature sensing indicating portion.

Further, the above-mentioned cover members 24, 25 may be formed of a heat insulation member so as to prevent, when touching the cover members with a finger, the heat of the finger from being easily transmitted to the capsules 28.

According to the present invention, the member base 13 is provided, for sandwiching and holding the above-mentioned label components 21 under a state in which the drawn-out portions on their one end side are protruded outward.

That is, the member base 13 includes the upper base member 11 and the lower base member 12 formed of two plate-like members. As illustrated in FIG. 1 to FIG. 3, in the upper base member 11 and the lower base member 12, the lower base member 12 includes convex portions 16 on part thereof, and forms spaces each having substantially a convex shape therein in combination of the upper base member 11. Further, the upper base member 11 and the lower base member 12 are configured to sandwich the label components 21 under a state in which the protruding portion 27 housing the capsules 28 of the label components 21 are received in the spaces for holding and protection.

In FIG. 1, reference numerals 14, 15 denote weld bonding portions for welding and bonding the upper base member 11 and the lower base member 12 together by, for example, ultrasonic waves. Here, in this embodiment, as is apparent from FIG. 1, five label components 21 are mounted in a parallel state, and portions other than label-component mounting portions are bonded together. Note that, it is preferred that weld bonding be performed in the above-mentioned bonding portions 14, 15 as described in this embodiment, but the present invention is not limited thereto. Adhesion or the like may be performed for bonding.

Further, in this embodiment, the upper base member 11 includes a protruding bent portion 31 formed therein, and the lower base member 12 includes a protruding bent portion 32 formed therein. When coupling the upper base member 11 and the lower base member 12 together, in each of the label components 21, the bent portions 31, 32 form a portion that is bent and held between the housing portion housing the capsules 28 and the drawn-out portion.

The bent portions 31, 32 described above increase rigidity of the member base, and reliably crush and break the capsules 28 by causing the capsules 28 to pass through a narrow gap through a pulling-out operation.

The temperature sensitive indicator 10 having the above-mentioned configuration is stored in a preparatory state by, for example, previously refrigerating the entire temperature sensitive indicator to service temperature or less.

Then, for use, one label component to be used is pulled out of the member base 13, and is attached to and enclosed in, for example, a cooling box storing the object to be measured. Note that, the label component may be pasted to a product or commercial item after peeling the release paper 26, etc.

In particular, according to the present invention, at the time of the above-mentioned pulling out, the capsules 28 are compressed and deformed in the convex (space) portion 16 on the member base 13 side, to thereby be crushed and broken. Further, the capsules 28 are crushed as described above, to thereby enter a preparatory state for measurement.

In this case, the label component does not develop color just by crushing the capsules 28, but monitors temperature by being attached to the object to be measured after the crushing.

For example, color development is confirmed after transportation of the object to be measured. If the label component does not develop color, it can be confirmed that the temperature does not reach to a predetermined temperature or more, and a certain period of time or more does not elapse.

On the other hand, if the label component develops color, it can be confirmed that a problem such as a temperature increase arises during delivery and the like. Therefore, the temperature sensitive indicator is suitably used for commercial items and products such as fresh goods including fresh food and cut flowers, medical goods, and semiconductor materials, which are degraded in quality if not undergoing sufficient temperature control and if being exposed to a predetermined temperature or more.

According to the above-mentioned configuration, the member base 13 including the upper base member 11 and the lower base member 12 is used as a case for storage, and an arbitrary one of the label components 21 is pulled out of the member base 13 for use. Thus, the capsules 28 are broken to enter a preparatory state for measurement. Therefore, despite the simple configuration, unlike the conventional case, it is not necessary to crush and break the capsules with a finger or the like when setting the temperature sensitive indicator 10, and the temperature of the finger or the like does not affect the temperature sensitive material. Consequently, more precise temperature measurement is possible.

Further, in the member base 13, the convex portions 16 for holding and protecting the capsules 28 are formed integrally with the lower base member 12, which is advantageous in enabling a reduction of the number of components, etc. Moreover, the convex portions 16 of the member base have such a functional advantage as to have two functions: holding and protection of the capsules 28 on the label component 21 side; and breaking the capsules 28.

Still further, as in this embodiment, the plurality of label components 21 are held in parallel to one another in the member base 13. Accordingly, the temperature sensitive indicator achieves the shared use of the case itself. Thus, the temperature sensitive indicator of the present invention is not only advantageous in terms of the number of components and cost, but also excellent in assembly property, usability, and the like.

Further, in the structure in which the label components 21 are provided in parallel to one another, the member base 13 is increased in size, and hence is easily held by hand when pulling out the label, and also advantageous in enabling a reduction of scraps at the time of disposal, etc.

Further, in the above-mentioned structure, the bent portions 31, 32 are provided in such a direction as to cross the label components 21 of the member base 13. Consequently, the rigidity of the member base 13 is increased, a degree of adhesion between the upper base member 11 and the lower base member 12 is improved, and a clearance (gap) is eliminated even when reducing the bonding portions between the upper base member 11 and the lower base member 12. Further, in this configuration, the capsules 28, which have not been able to be broken when pulling out the label component 21, can also be broken by causing the label component 21 to pass through the bent portions 31, 32, and hence are broken more reliably.

FIG. 3 illustrates the above-mentioned state in which the capsules 28 held and protected in the protrusion 27 on the label component 21 side are crushed in the convex portion 16 on the member base 13 side. It is easily understood that, by pulling out the label component 21 in a pulling-out direction, the capsules 28 are compressed and deformed in the convex portion 16 and gradually crushed, to thereby be broken.

That is, the label component 21 pulled out of the member base 13 is attached to the object to be measured by pasting or the like so as to check a temperature change. Then, when the temperature reaches to a predetermined temperature or more, or a predetermined period of time elapses, the temperature sensitive material gradually permeates the absorbent paper 23 to spread along a longitudinal direction of the absorbent paper 23 from the position at which the capsules 28 are placed. At this time, it is only necessary that a state of color development can be confirmed through a color development indicating portion M as a window portion provided in the upper cover member 24 formed of, for example, an opaque sheet.

In other words, at a desired set temperature or more, the internal temperature sensitive material (wax, etc.) melts to develop color such as red, and it is possible to know the lapse of time based on a range (distance) at which the temperature sensitive material permeates the absorbent paper 23 (permeable material) of the label component 21. That is, even if the absorbent paper 23 partially develops color, there is no problem if the color development indicates that the lapse of time is within a certain range, and its confirmation can be performed. Further, the label component is formed by pasting a nontransparent and opaque sheet on part of the surface of the label component 21 made of a transparent material. However, by making part of the opaque sheet transparent as the color development indicating portion M by forming the window portion or the like, it is possible to confirm color development of the temperature sensitive material absorbed by the absorbent paper 23, and to confirm the fact that a certain period of time or more elapses.

Note that, the present invention is not limited to the structure described in the above-mentioned embodiment, and it is needless to say that the shape, structure, and the like of each component forming the temperature sensitive indicator 10 may be appropriately modified and changed.

For example, in the above-mentioned embodiment, description is made of the case where the plurality of (five) label components 21 are held in parallel to one another along one side of the member base 13 while being sandwiched between the upper base member 11 and the lower base member 12, but the present invention is not limited thereto. There may be conceived various modified examples, such as a configuration in which a plurality of label components are arranged in parallel to one another on each side of the member base, and the label components are allowed to be pulled out of the member base for use.

Further, in the above-mentioned embodiment, the adhesive layer is provided in the member base 13 of the label component 21, and by peeling the release paper 26 pasted to the adhesive layer, the label component 21 can be pasted to the object to be measured. However, the present invention is not limited thereto. The label component 21 may be stored in a cooling box, a stockroom, or the like together with the object to be measured. That is, the label component 21 only needs to be attached so as to allow confirmation of a condition of the temperature of the object to be measured.

Further, the convex portions 16 formed on the lower base member 12 may be provided on the upper base member 11 side, or may be formed by the upper base member 11 and the lower base member 12.

In addition, the present invention is not limited to the case where the bent portions 31, 32 form a bent path having a small width as in the above-mentioned embodiment. A bent space may be formed by bending any one of the upper base member 11 and the lower base member 12 and leaving the other flat.

Further, there may be conceived modified examples, such as a configuration in which the rigidity of the base members 11, 12 is increased by folding and forming the end portions of the upper base member 11 and the lower base member 12.

Figure 4:
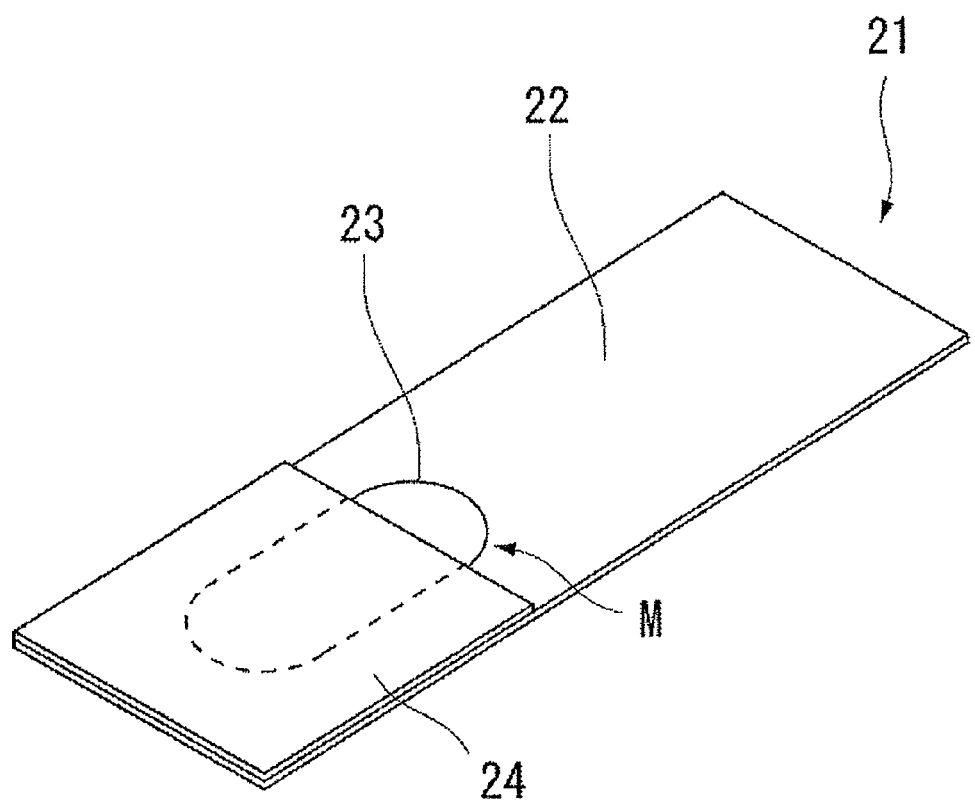
FIG. 4 A view illustrating a modified example of a detection indicating state indicated by the label component drawn out in the temperature sensitive indicator according to the present invention.

Further, the color development indicating portion M is not limited to the window portion described above. As illustrated in FIG. 4, the upper cover member 24, which is formed of an opaque sheet and provided by being laminated on the sheet member 22 formed of a transparent sheet, is formed to have such a length as to expose the end portion of the absorbent paper 23 to the outside. In this manner, the exposed end portion of the absorbent paper 23 may be used as the color development indicating portion M as the window portion.

This is advantageous in achieving a cost reduction and the like by reducing material cost. Here, FIGS. 6(a) and 6(b) illustrate an example in which a label for freezing and a label for refrigeration are distinguished from each other based on, for example, whether or not a V-shaped cut is provided at an end portion of the label.

INDUSTRIAL APPLICABILITY

The temperature sensitive indicator according to the present invention is suitably used in fields of production, delivery, and storage of products and commercial items, such as fresh food, frozen food, cut flowers, medical goods, and semiconductor materials, which need to be controlled in temperature.

REFERENCE SIGNS LIST 10 temperature sensitive indicator
11 upper base member
12 lower base member
13 member base
14, 15 weld bonding portion (bonding portion)
16 convex portion
21 label component
22 transparent sheet (sheet member)
23 absorbent paper (absorbent member)
24 upper opaque sheet (upper cover member)
25 lower opaque sheet (lower cover member)
26 release paper
27 protrusion
28 wax (temperature sensitive material)
31, 32 bent portion
M color development indicating portion

The invention claimed is:
1. A temperature sensitive indicator, comprising:
 a member base including an upper base member and a lower base member; and
 a label component, one end of which is sandwiched and held between the upper base member and the lower base member of the member base and another end of the label component is protruded outward, the label component comprising:
 a sheet member;
 an absorbent member provide on an upper part of the sheet member;
 a capsule placed on one end side of the absorbent member and containing a temperature sensitive material that melts at a predetermined temperature or more which is the temperature at which the temperature sensitive material melts into a liquid; and a cover member including a protrusion covering the capsule, wherein the protrusion of the cover member is held inside the member base, housed in a convex portion provided on any one of or both of the upper base member and the lower base member, and wherein, by pulling the another end of the label component out of the member base, the capsule is pressed in the convex portion of the lower base member and is broken to enter a preparatory state for measurement, and the temperature sensitive material melts into a liquid at the predetermined temperature or more so that the liquid is absorbed by the absorbent member and turns color, thereby coloring the absorbent member and enabling confirmation that the temperature sensitive indicator senses a temperature equal to or greater than the predetermined temperature through confirmation of the coloring of the absorbent member by the liquid, the upper base member and the lower base member each comprising a bent portion provided between the convex portion of the member base and a side end portion of the member base from which the pulled-out portion of the label component protrudes.

2. A temperature sensitive indicator according to claim 1, wherein the label component comprises a plurality of label components set in the member base, and wherein one of the plurality of label components is pulled out for use, and is attached to an object to be measured.

\* \* \* \* \*